(12) United States Patent
Meyer et al.

(10) Patent No.: US 12,096,914 B2
(45) Date of Patent: Sep. 24, 2024

(54) ENDOSCOPIC SYSTEM INCLUDING FILTER ASSEMBLY

(71) Applicant: KARL STORZ Imaging, Inc., Goleta, CA (US)

(72) Inventors: William H. Meyer, Ventura, CA (US); Christopher Zimmer, Santa Barbara, CA (US)

(73) Assignee: KARL STORZ Imaging, Inc., Goleta, CA (US)

( * ) Notice: Subject to any disclaimer, the term of this patent is extended or adjusted under 35 U.S.C. 154(b) by 0 days.

(21) Appl. No.: 18/500,655

(22) Filed: Nov. 2, 2023

(65) Prior Publication Data
US 2024/0057854 A1 Feb. 22, 2024

Related U.S. Application Data

(63) Continuation of application No. 17/068,191, filed on Oct. 12, 2020, now Pat. No. 11,839,357.

(51) Int. Cl.
*A61B 1/00* (2006.01)
*G02B 23/24* (2006.01)
*G02B 5/26* (2006.01)

(52) U.S. Cl.
CPC ...... *A61B 1/00186* (2013.01); *A61B 1/00064* (2013.01); *G02B 23/2453* (2013.01); *G02B 23/2484* (2013.01); *G02B 5/26* (2013.01); *G02B 23/2446* (2013.01)

(58) Field of Classification Search
CPC . A61B 1/00186; A61B 1/00064; A61B 1/042; G02B 23/2453; G02B 23/2484; G02B 5/26; G02B 23/2446; G02B 5/22
See application file for complete search history.

(56) References Cited

U.S. PATENT DOCUMENTS 5,833,596 A * 11/1998 Bonnell ............ G02B 23/2407
250/353

\* cited by examiner

*Primary Examiner* — James C. Jones
(74) *Attorney, Agent, or Firm* — David N. Villalpando

(57) ABSTRACT

A filter assembly is configured to optically couple a camera head to an endoscope. The filter assembly includes a first end adapted to be removably coupled to the camera head and a second end opposite and spaced apart from the first end, the second end adapted to be removably coupled to the endoscope. The filter assembly includes an optic housing disposed between the first end and the second end, the optic housing includes an optical path length maximizer and a first window. The first window has a first surface that is angled with respect to a plane that is perpendicular to a longitudinal axis of the optic housing so as to minimize a narcissus reflection within the optic housing and an optical filter to reject laser irradiation.

20 Claims, 3 Drawing Sheets

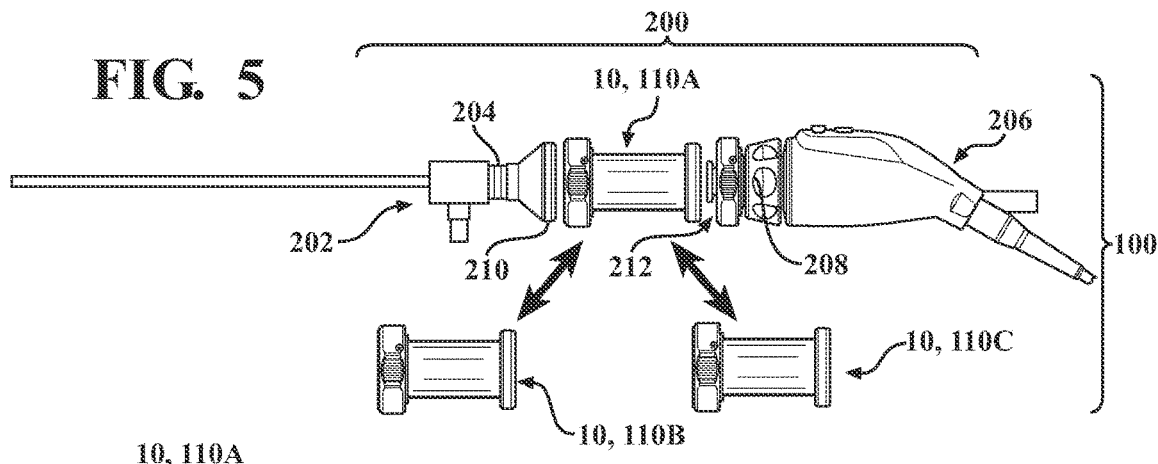
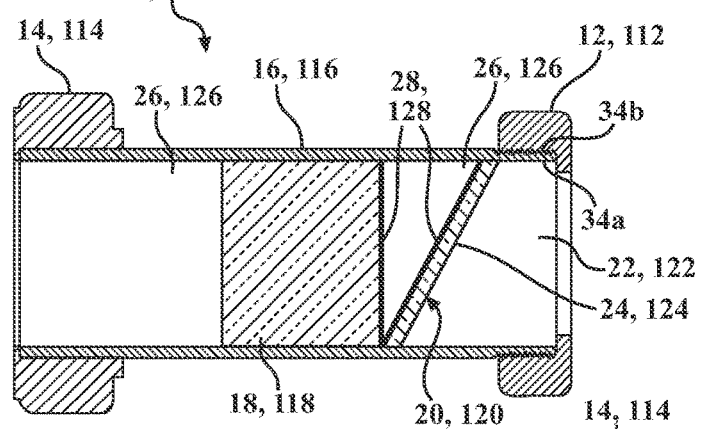
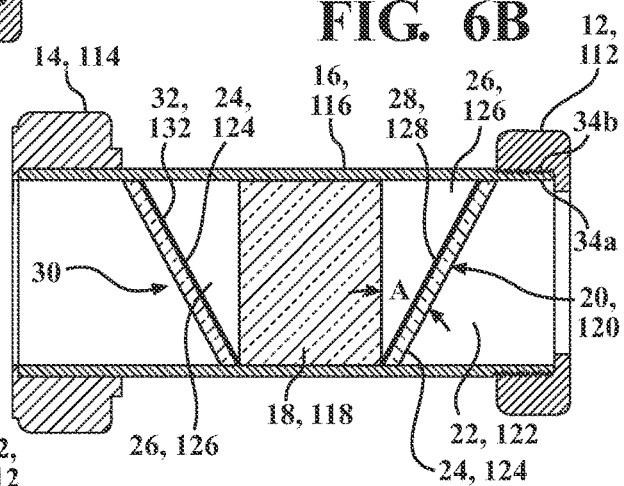
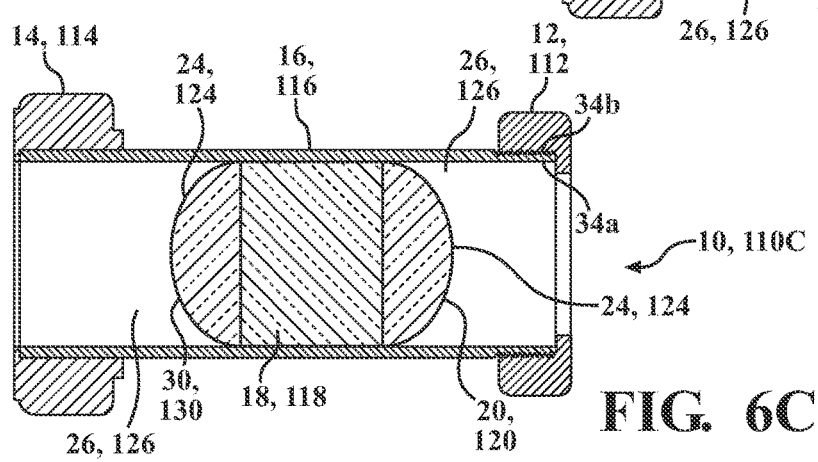

ously mounted to the camera head. FIG. 1 depicts the endoscope 302 having a mounting feature disposed on a proximal end. The mounting feature is adapted to engage gripping mechanism of the camera head. When mounted, the endoscope is positioned with respect to the image sensor so as to provide a focused image.

ENDOSCOPIC SYSTEM INCLUDING FILTER ASSEMBLY

CROSS-REFERENCE TO RELATED APPLICATION

This application is a continuation of U.S. patent application Ser. No. 17/068,191, filed on Oct. 12, 2020, and entitled "Filter Assembly and Filter Kit for Use with an Endoscopic System," the content of which is incorporated herein by reference in its entirety.

TECHNICAL FIELD

The disclosure relates to a filter as part of an endoscopic system.

BACKGROUND

Endoscopic systems 300 are used for surgical procedures. The endoscopic system 300 provides a video or camera image of a surgical site. The endoscopic system 300 includes a camera head 306 having an image sensor 308 and an endoscope 302 having a lens 304. An illustrative example of an endoscopic system is provided in FIG. 1.

The endoscope 302 is configured to be removably mounted to the camera head. FIG. 1 depicts the endoscope 302 having a mounting feature disposed on a proximal end. The mounting feature is adapted to engage gripping mechanism of the camera head. When mounted, the endoscope is positioned with respect to the image sensor so as to provide a focused image.

Some endoscopic procedures use lasers to treat medical conditions such as controlling hemorrhaging or destroying neoplastic tissue. Laser irradiation may generate a very large signal level which can saturate a camera's image. Thus, certain endoscopic systems include filters for reducing the laser signal level. Many types of lasers may be used, each emitting light within a narrow wavelength band. This requires multiple endoscopic systems having many endoscopes or many camera heads, each with a corresponding filter to block the reflected light within the narrow wavelength band.

SUMMARY

One aspect of the disclosure provides an endoscopic system having a filter assembly. The filter assembly is configured to optically couple a camera head to an endoscope. The filter assembly includes a first end that is adapted to be removably coupled to the camera head. The filter assembly includes a second end that is opposite of the first end and spaced apart therefrom. The second end is adapted to be removably coupled to the endoscope. Accordingly, the filter couples the camera head to the endoscope.

The filter assembly includes an optic housing. The optic housing is disposed between the first end and the second end. An optical path length maximizer is housed within the optic housing. The optical path length maximizer is configured to compensate for the displacement of the exit pupil of a lens system of an attached endoscope relative to the image sensor so as to maintain the field of view and optical quality of the optical image while accommodating a laser filter.

The optic housing further includes a first window. The first window has an operating surface configured to reflect an image away from a longitudinal axis of the optic housing. In one aspect, the operating surface is an angled surface with respect to a plane that is perpendicular to a longitudinal axis of the optic housing so as to minimize a narcissus reflection when working with the camera image sensor.

In one aspect of the filter assembly, the filter assembly includes a first coating. The first coating is configured to filter a first pre-determined wavelength of light so as to prevent the pre-determined wavelength of light from reaching the camera head.

In another aspect of the filter assembly, the first coating is disposed on one of either the optical path length maximizer or the first window.

In yet another aspect of the disclosure, the filter assembly includes a second window disposed within the optic housing. The second window is spaced apart from the first window, and the second window is angled with respect to the plane that is perpendicular to the longitudinal axis of the optic housing.

In yet another aspect of the disclosure, the first and second ends are removably attached from the optic housing so as to allow the user to change or replace a respective first or second window as the case may be.

In yet another aspect of the disclosure, a filter kit is provided. The filter kit is configured to optically couple a camera head to an endoscope. The filter kit includes a plurality of filters, each of the filters having a first end, a second end and an optic housing. Wherein, the first end is adapted to be removably coupled to the camera head, and the second end is opposite and spaced apart from the first end, and the second end is adapted to be removably coupled to the endoscope. In such an aspect, each of the first and second ends are the same in structure with each other so as to be interchangeable with respect to a predetermined camera head and a predetermined endoscope.

The optic housing of each of the filters is disposed between the first end and the second end of the optic housing and includes a first window. The first window is angled with respect to the plane that is perpendicular to the longitudinal axis of the optic housing In such an embodiment, the first window includes a first coating configured to filter a predetermined wave length of light from reaching the camera head, wherein the first coating filters a predetermined wavelength of light different from each other.

In yet another aspect of the filter kit, the first windows of each of the plurality of filters may be angled differently from each other.

In yet another aspect of the filter kit, a second window may be provided. The second window is also angled with respect to the plane that is perpendicular to the longitudinal axis of the optic housing. The details of one or more implementations of the disclosure are set forth in the accompanying drawings and the description below. Other aspects, features and advantages will be apparent from the description and drawings and from the claims.

BRIEF DESCRIPTION OF THE DRAWINGS

The embodiments set forth in the drawings are illustrative and exemplary in nature and not intended to limit the subject matter defined by the claims. The following description of the illustrative embodiments can be understood when read in conjunction with the following drawings, where like structure is indicated with like reference numerals and in which:

FIG. 5 is a view of an endoscopic system and a filter kit in accordance with one or more embodiments illustratively described herein.

FIG. 6A is a perspective view and cross-section view of a first filter assembly of the filter kit shown in FIG. 5.

FIG. 6B is a perspective view and cross-section view of a second filter assembly of the filter kit shown in FIG. 5.

FIG. 6C is a perspective view and cross-section view of a third filter assembly of the filter kit shown in FIG. 5.

DETAILED DESCRIPTION OF PREFERRED EMBODIMENTS

Figure 3:
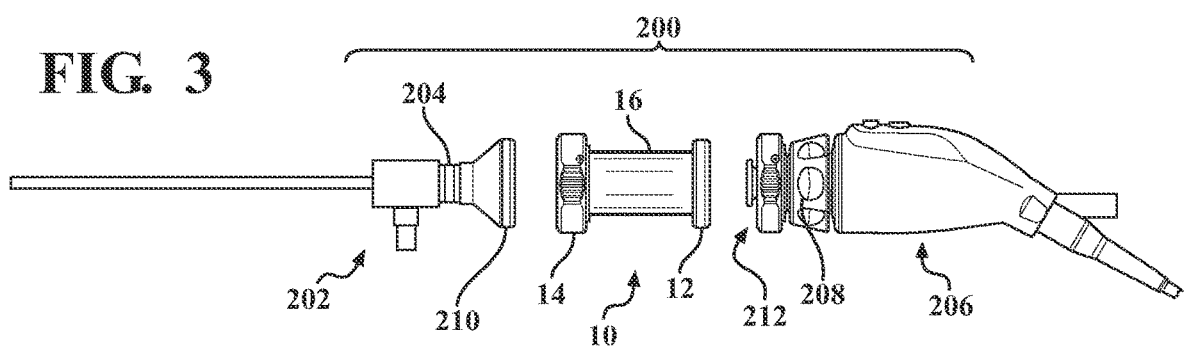
FIG. 3 is an exploded view of an endoscopic system in accordance with one or more embodiments illustratively described herein.

Implementations herein are directed toward a filter assembly and a filter kit. The filter assembly is configured to removably and optically couple a camera head to an endoscope. The filter assembly includes one or more features to block reflected light from one or more lasers emissions within predefined wavelength bands. The filter assembly kit may include a plurality of filter assemblies, each capable of blocking a different band of wavelengths. Each filter assembly also includes one or more features to reduce a narcissus phenomenon caused by self-imaging of the image sensor. As shown in FIG. 3, the endoscope is configured to attach to a camera head. In such a configuration, the focal point of the camera head is based upon the distance of the lens with respect to the image sensors of the camera head. Thus, when mounted together the camera view is in focus. It should be appreciated that the displacement of the endoscope and the lens therein from the image sensor defocuses the camera image. Thus, in such an embodiment, the endoscope system may obtain a blurry image when used in a procedure involving laser beams.

As such, a filter assembly is provided herein which has an optical path length maximizer configured to compensate for the displacement of the exit pupil of the lens system of the endoscope with respect to the image sensor so as to maintain the field of view and optical quality of the optical image. Furthermore, the filter assembly includes a window configured to have an angled or arcuate surface so as to reflect the re-image of the sensor surface and reduce narcissus reflection.

Figure 1:
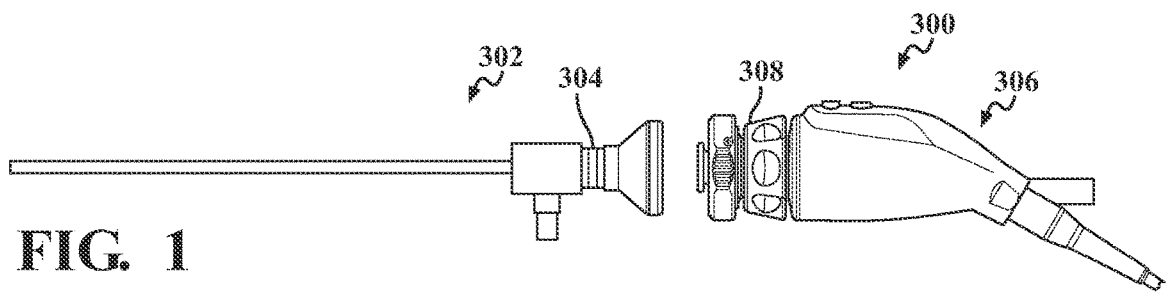
FIG. 1 is a perspective view of an endoscopic system of the prior art.
Figure 2:
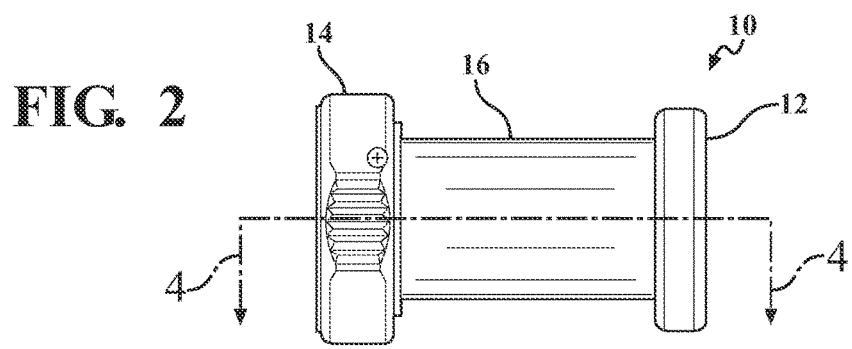
FIG. 2 is a perspective view of a filter assembly in accordance with one or more embodiments illustratively described herein.

With reference now to FIG. 2 a perspective view of the filter assembly 10 is provided. The filter assembly 10 is configured to be used with an endoscopic system 200. The endoscopic system 200 includes an endoscope 202 having a lens 204 fixed therein and a camera head 206 having an image sensor 208 fixed therein. The filter assembly 10 includes a first end 12 adapted to be removably coupled to the camera head 206 and a second end 14 opposite and spaced apart from the first end 12. The second end 14 is adapted to be removably coupled to the endoscope 202.

With reference now to FIG. 3, an illustrative depiction of an endoscopic system 200 is provided. The endoscope 202 includes a mating end, commonly referenced as an eyecup 210, which is configured to be seated within an endoscope gripping mechanism 212 of the camera head 206, placing the lens 204 of the endoscope 202 in a set distance with the image sensor 208 of the camera head 206 so as to place the camera image in focus.

FIG. 3 also shows how the endoscopic system 200 may be configured such that the endoscope 202 is directly attached to the camera head 206, or the endoscope 202 may be released from the camera head 206 and filter assembly 10 disposed between the endoscope 202 and the camera head 206. In particular, the first end 12 of the filter assembly 10 is shown having the same dimension as the eyecup 210 of the endoscope 202 and the second end 14 of the filter assembly 10 is shown having the same dimension as the endoscope gripping mechanism 212 of the camera head 206.

FIG. 3 illustrates how the endoscopic system 200 may be used with or without the filter assembly 10. Thus, the endoscopic system 200 may be adapted for use in surgical procedures utilizing lasers. It should be appreciated that the dimension of the first and second ends 12, 14 of the filter assembly 10 shown in the drawings are for illustrative purposes and may be shaped otherwise so as to mimic the shape of the eyecup 210 and an endoscope gripping mechanism 212 of the respective endoscope 202 and camera head 206.

Figure 4:
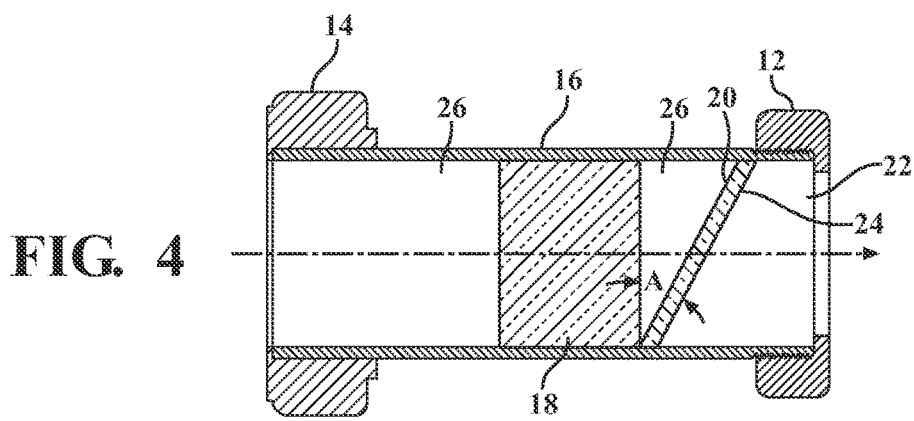
FIG. 4 is a cross-sectional view of FIG. 2 taking along lines 4-4.
Figure 7A:
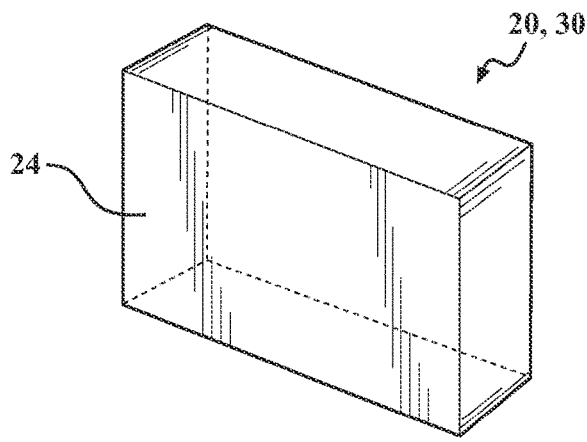
FIG. 7A is an illustrative view of a first or second window being a planar surface having a cuboidal dimension.
Figure 7B:
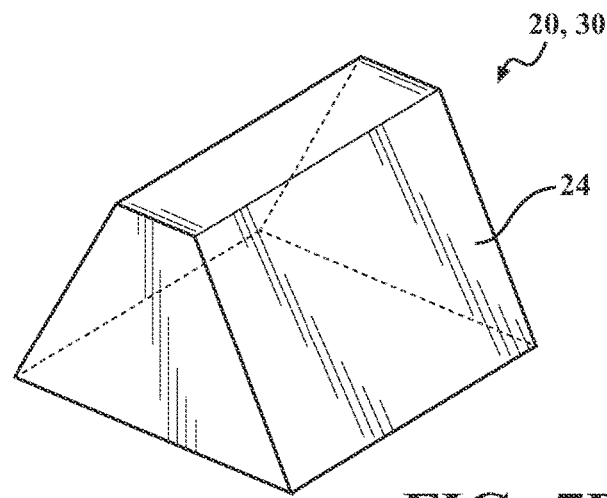
FIG. 7B is an illustrative view of a first or second window being a triangular prism.
Figure 7C:
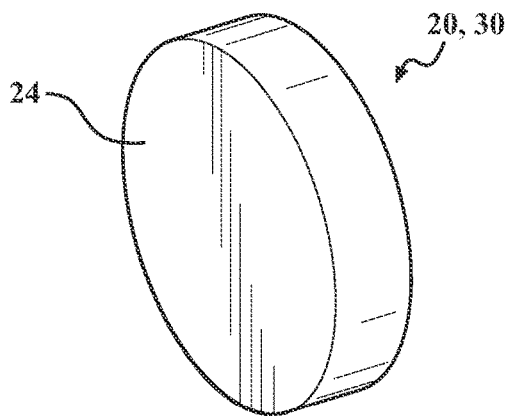
FIG. 7C is an illustrative view of a first or second window being a planar surface having a cylindrical dimension.
Figure 7D:
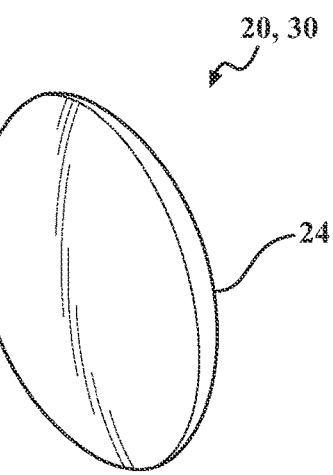
FIG. 7D is an illustrative view of a first or second window having an arcuate surface.

With reference again to FIG. 2 and now also to FIG. 4, a description of the filter assembly 10 is provided. The filter assembly 10 is optically coupled between the endoscope 202 and the camera head 206. The filter assembly 10 is configured to compensate for the displacement of the exit pupil of the lens 204, accommodating for a displacement of the lens 204 with respect to the image sensor 208 so as to maintain the field of view and optical quality of the optical image.

The filter assembly 10 includes an optic housing 16. The optic housing 16 is disposed between the first end 12 and the second end 14. The optic housing 16 includes an optical path length maximizer 18 and at least a first window 20. The optic housing 16 may be a generally tubular member having a through-hole 22. The optical path length maximizer 18 is disposed within the through-hole 22 and is generally centered between the first and second ends 12, 14. The opposing ends of the optic housing 16 are spaced apart from respective first and second ends 12, 14 so as to accommodate the first window 20.

The optical path length maximizer 18 may be a relay optic or high glass index. The optical path length maximizer 18 is configured to compensate for the displacement of the exit pupil of the lens 204 so as to maintain the field of view and optical quality of the optical image detected by the camera when the lens 204 is displaced from the camera head 206. The optical path length maximizer 18 may be formed of a cylinder of high index of refraction optical material such as sapphire or another lens relay assembly.

The first window 20 is configured to reduce a narcissus reflection, in particular the first window includes a surface 24 configured to reflect laser light away from a longitudinal axis of the optic housing 16. In one aspect, the filter assembly may include a second window 30 that is also configured reflect laser light away from a longitudinal axis of the optic housing 16. The first window 20 and second window 30 may be formed of any durable optical material compatible with necessary coatings and human tissue contact.

With reference now to FIG. 4, a cross-sectional view of the filter assembly 10 is provided. The optical path length maximizer 18 is shown generally centered within the optic housing 16. A gap 26 is formed between opposite ends of the optical path length maximizer 18 and the respective first and second ends 12, 14 of the filter assembly 10. One of the gaps 26 is dimensioned to accommodate a first window 20.

The cross-sectional view provides an illustrative depiction of the first window 20 with respect to the optical path length maximizer 18. The surface 24 of the second window 30 is illustratively shown as being an angled surface of approximately 20 degrees, (a tilt angle "A") with respect to a plane that is perpendicular to a longitudinal axis of the optic housing 16. However, it should be appreciated that the tilt angle "A" of the surface 24 may be anywhere between 10 degrees to 45 degrees, depending on the desired reflection, or the surface 24 may be curved.

The dashed arrow indicates an optical path for light that pass through the lens 204. In particular, the lens 204 disposed on the endoscope 202 reflects the light down a longitudinal path which is defined by the axial length of the optic housing 16. When used in a laser procedure, light from the laser beam passes through the second window 30 and is reflected away from the camera head 206 as illustrated by the solid arrow. In particular, the light from the laser beam is reflected at an angle of incidence determined by the tilt of the window 30.

With reference now to FIG. 6A, an aspect of the filter assembly 10 having a first coating 28 is provided. The first coating 28 is configured to filter a first predetermined wavelength of light so as to prevent the first predetermined wavelength of light from reaching the camera head 206. In particular, the first coating 28 may be configured to filter a laser having a center wavelength or approximately 1064 nm as may be found in a Nd:YAG laser or any standard ion laser having wavelengths within the visible and ultraviolet spectra, for example centered about 351.1 nm, 363.8 nm, 454.6 nm, 457.9 nm, 465.8 nm, 476.5 nm, 488.0 nm, 496.5 nm, 501.7 nm, 514.5 nm, 528.7 nm, and 1092.3 nm. Such coatings are currently known and used, and any such coating may be adapted for use herein. FIG. 5 shows the first coating 28 disposed on both the end surface of the optical path length maximizer 18 and the first window 20. However, it should be appreciated that the first coating 28 may be disposed on just one of either the optical path length maximizer 18 or the first window 20.

The first coating 28 can be placed on any or all of the internal optical surfaces. Preferably, the first coating 28 is disposed on an interior surface of the first window 20. FIG. 6A illustrates an example where the first coating 28 is disposed on the surface of the optical path length maximizer 18 facing the first window 20. It should be appreciated that the first coating 28 may be disposed on a single surface and is shown as being on both the optical path length maximizer 18 and the first window 20 for illustrative purposes.

FIG. 6B discloses another aspect of the filter assembly 10, wherein the filter assembly 10 includes the second window 30. The second window 30 also includes a surface 24 that is configured to direct light away from the longitudinal axis of the optic housing 16.

The second window 30 is disposed within the optic housing 16. FIG. 6B shows the second window 30 disposed on one end of the optic housing 16 opposite of the first window 20. The first surface 24 of the first window 20 and the second window 30 may be an angled surface angled the same as each other but symmetrical to each other. However, it should be appreciated that the first surface 24 of the first and second windows 30 may be angled differently from each other or may be oriented in the same direction.

The use of a second window 30 may help further reduce narcissus effect. The second window 30 may further include a second coating 32. The second coating 32 may be configured to filter a second predetermined wavelength of light, the second predetermined wavelength of light being different than the first predetermined wavelength of light.

As such, the advantages of having a second coating 32 allows for the filter assembly 10 to be used for different laser procedures. For instance, some surgical procedures may utilize a laser having a center wavelength of 454.6 nm, whereas another surgical procedure may use a laser having a center wavelength of 476.5 nm. Assuming the first coating 28 filters a center wavelength of 454.6 nm and the second coating 32 filters a center wavelength of 476.5 nm, it should be appreciated that the same filter assembly 10 may be used for either surgical procedure, thus eliminating the need to use a separate endoscopic system 200 for each respective surgical procedure.

With reference now to FIGS. 6A-6B, another aspect of the filter assembly 10 is provided wherein the first and second ends 12, 14 are configured to be removably attached to the optic housing 16. In such an embodiment, the first and second ends 12, 14 may be threaded onto the optic housing 16 as indicated by the threads 34a disposed on the ends of the optic housing 16, wherein the first and second ends 12, 14 have a threaded bore 34b so as to be simply screwed onto the ends of the optic housing.

Alternatively, a snap fit engagement may be used to couple the two parts together. It should be appreciated that any known fastening mechanism may be used to removably attach the first and second ends 12, 14 to the optic housing 16. In such an embodiment the removal of the first or second ends 12, 14 provide access to the optic housing 16 so as to allow the user to change or replace any of the first or second windows 20, 30 with a different window so as to facilitate cleaning of the filter assembly 10 and also allow the filter assembly 10 to operate in various conditions with laser of different wavelengths.

With reference now to FIG. 5 a perspective view of a filter kit 100 is provided, wherein like elements are referenced by the same number increased by 100. The filter kit 100 includes a plurality of filter assemblies 110 as described above. For illustrative purposes, the filter kit 100 is shown as having three filter assemblies 110a, 110b, 110c. The bi-directional arrow indicates that the filter assemblies 110a, 110b, 110c may be interchanged. Accordingly, each filter assembly 10 includes a first end 112 adapted to be removably coupled to the camera head 206 and a second end 114 opposite and spaced apart from the first end 112. The second end 114 is adapted to be removably coupled to the endoscope 202.

With again to FIGS. 6A-6C a cross-sectional view of exemplary filter assemblies 110 to be used in a filter kit 100 is provided. Each filter assembly 110 is configured to compensate for the displacement of the exit pupil of the lens 204 so as to maintain the field of view and optical quality of the optical image detected by the camera accommodating for a displacement of the lens 204 with respect to the image sensor 208. However, the components of a respective filter assembly 110 are different from each other so as to achieve a specific optical function. For instance, each of the filter assemblies 110a, 110b, 110c may be used for a laser operation having a laser generating light in different wavelength spectrums. It should be appreciated that a particular filter assembly may be configured to be used for procedures implementing multiple laser wavelengths. For example, filter assembly 110b is shown as having both the first and second coating 128, 132.

Each filter assembly 110 includes an optic housing 116. The optic housing 116 is disposed between the first end 112 and the second end 114. The optic housing 116 includes an optical path length maximizer 118 and a first window 120. The optic housing 116 may be a generally tubular member having a through-hole 122. The optical path length maximizer 18 is disposed within the through-hole 122 and is generally centered between the first and second ends 112, 114. As discussed above, the optical path length maximizer 118 may be a relay optic or high glass index. The optical path length maximizer 118 is configured to compensate for the displacement of the exit pupil of the lens 204 so as to maintain the field of view and optical quality of the optical image detected by the camera when the lens 204 is displaced from the camera head 206. The optical path length maximizer 118 as realized as a relay optic as in FIG. 6C may be formed of conventional optical glass materials and processes (BK7 for example).

With reference first to FIG. 6A, the filter assembly 110a includes a first window 120. The first window 120 has a first surface 124 configured to reflect light away from a longitudinal axis of the optic housing 116 so as to minimize the narcissus reflection within the optic housing 116. The first coating 128 is configured to filter a first predetermined wavelength of light from reaching the camera head 206. In particular, the first coating 128 may be configured to filter a wavelength between 400 nm to 2000 nm. As described above, such coatings are currently known and used, and any such coating may be adapted for use herein, illustratively including multilayer dielectric coatings.

FIG. 6B depicts a filter assembly 110b of the filter kit 100 having a first window 120 and a second window 130, both of which are configured to reflect light away from a longitudinal axis of the optic housing 116 so as to minimize the narcissus reflection within the optic housing 116. The second window 130 includes a second coating 132. The second coating 132 may be configured to filter a predetermined wavelength of light different than the first coating 128. Such a filter assembly 110b may be useful in surgeries where two to more different laser procedures are implemented.

FIG. 6C depicts a filter assembly 110c of the kit having a first window 120 and a second window 130. The first surface 124 of the first window 120 is arcuate. The first coating 128 is shown disposed on an inner surface of the first window 120. The second window 130 is arcuate so as to preserve the focus of the image transmission.

It should be appreciated that the filter assemblies 110a, 110b, 110c shown in FIGS. 6A-6C are illustrative and not limiting to the scope of the appended claims. The filter assemblies 110a, 110b, 110c provide optical benefits different from each other that are suitable for different laser procedures. Accordingly, the filter kit 100 may be configured with filter assemblies other than what is shown in the figures without deviating from the scope of the appended claims. For instance, the filter assemblies may be configured to have a first end 112 and a second end 114 that is removable.

It should further be appreciated that the shape and dimension of the first window 120 and the second window 130 are provided for illustrative purposes and other shapes may be used to perform the function of directing light away from the longitudinal axis of the optic housing 16. For instance, FIGS. 7A-7D show different window shapes that may be incorporated herein. Each of the shapes having a first surface 24 that is configured to reflect an image on the respective window away from the longitudinal axis of the optic housing 16.

A number of implementations have been described. Nevertheless, it will be understood that various modifications may be made without departing from the spirit and scope of the disclosure. Accordingly, other implementations are within the scope of the following claims.

The invention claimed is:

1. An endoscopic system comprising:
   an endoscope with a lens system and an exit pupil of said endoscopic lens system;
   a filter assembly;
   a camera head releasably connectable to the endoscope or to the filter assembly, the camera head comprising an image sensor, wherein, when the camera head is connected to the endoscope, an in-focus image is received from the endoscope at the image sensor; and
   wherein the filter assembly is configured to optically couple the camera head to the endoscope, and the filter assembly comprises:
   a first end adapted to be removably coupled to the camera head;
   a second end opposite and spaced apart from the first end, the second end adapted to be removably coupled to the endoscope; and
   an optic housing disposed between the first end and the second end, the optic housing including an optical path length maximizer and a first window, the first window having a first surface that is angled with respect to a plane that is perpendicular to a longitudinal axis of the optic housing.

2. The endoscopic system of claim 1, wherein the filter assembly further includes a first coating configured to filter a first predetermined wavelength of light.

3. The endoscopic system of claim 1, wherein the optical path length maximizer is one of a relay optic or a high index glass.

4. The endoscopic system of claim 2, wherein the first window comprises the first coating.

5. The endoscopic system of claim 4, wherein the first predetermined wavelength of light is centered about 1064 nm.

6. The endoscopic system of claim 4, wherein the first predetermined wavelength of light is centered about 464.5 nm.

7. The endoscopic system of claim 4, wherein the first coating is disposed one of either the optical path length maximizer or the first window.

8. The endoscopic system of claim 4, wherein the filter assembly further comprises a second window disposed within the optic housing, the second window spaced apart from the first window, the second window being angled with respect to the plane that is perpendicular to the longitudinal axis of the optic housing.

9. The endoscopic system of claim 8, wherein the second window comprises a second coating configured to filter a second predetermined wavelength of light, the second predetermined wavelength of light being different than the first predetermined wavelength of light.

10. The endoscopic system of claim 9, wherein the second predetermined wavelength of light is centered around 476.5 nm.

11. The endoscopic system of claim 4; wherein the filter assembly further comprises a second window disposed within the optic housing, the second window spaced apart from the first window, the second window being angled with respect to the plane that is perpendicular to the longitudinal axis of the optical housing; wherein the second window comprises a second coating configured to filter a second predetermined wavelength of light, the second predetermined wavelength of light being different than the first predetermined wavelength of light; and wherein the first predetermined wavelength of light is centered about 464.5 nm, and the second predetermined wavelength of light is centered around 476.5 nm.

12. The endoscopic system of claim 4, wherein the first surface of the first window is not parallel to a second surface of the first window, the first and second surfaces of the first window being opposite each other and being surfaces through which light passes from the endoscope to the camera head.

13. The endoscopic system of claim 8, wherein the first surface of the second window is not parallel to a second surface of the second window, the first and second surfaces of the second window being opposite each other and being surfaces through which light passes from the endoscope to the camera head.

14. The endoscopic system of claim 8, wherein the first surface of the first window is not parallel to the first surface of the second window.

15. The endoscopic system of claim 4, wherein the first coating is disposed on a surface of the first window facing the optical path length maximizer.

16. The endoscopic system of claim 1, wherein at least one surface of the first window through which light may pass from the endoscope to the camera head is not planar.

17. The endoscopic system of claim 8, wherein at least one surface of the second window through which light may pass from the endoscope to the camera head is not planar.

18. The endoscopic system of claim 5, wherein the first coating is disposed on both an end surface of the optical path length maximizer and on a surface of the first window.

19. The endoscopic system of claim 3, wherein the optical path length maximizer is a relay optic, wherein the relay optic comprises the first window, and wherein the first window comprises a first coating deposited on a surface thereof, the first coating configured to filter a first predetermined wavelength of light.

20. The endoscopic system of claim 1, comprising a second filter assembly, the second filter assembly configured to optically couple the camera head to the endoscope, the second filter assembly being mechanically interchangeable with the first filter assembly, and comprising:
   a first end adapted to be removably coupled to the camera head;
   a second end opposite and spaced apart from the first end, the second end adapted to be removably coupled to the endoscope; and
   an optic housing disposed between the first end and the second end, the optic housing including an optical path length maximizer and a first window, the first window having a first surface that is angled with respect to a plane that is perpendicular to a longitudinal axis of the optic housing.

* * * * *